United States Patent

Hoerner

Patent Number: 5,443,526
Date of Patent: Aug. 22, 1995

[54] ADJUSTABLE PROSTHETIC CONNECTOR ASSEMBLY

[76] Inventor: Jeffery S. Hoerner, 1726 Sequoia Ct., Allentown, Pa. 18104

[21] Appl. No.: 267,493

[22] Filed: Jun. 29, 1994

[51] Int. Cl.⁶ .................. A61F 2/80; A61F 2/62
[52] U.S. Cl. ..................... 623/38; 411/531; 411/539; 411/540; 411/994
[58] Field of Search .............. 623/38; 411/531, 539, 411/540, 994

[56] References Cited

U.S. PATENT DOCUMENTS

| | | | |
|---|---|---|---|
| 413,269 | 10/1889 | Tyson | 411/994 |
| 1,033,677 | 7/1912 | Day | 411/539 |
| 3,273,168 | 9/1966 | Gardner et al. | |
| 3,414,908 | 12/1968 | Waggott et al. | 623/38 |
| 3,422,462 | 9/1969 | Finnieston | 623/38 |
| 3,597,767 | 8/1971 | Prahl | 623/38 |
| 4,883,494 | 11/1989 | Cooper | |
| 4,938,775 | 7/1990 | Morgan | |
| 4,969,911 | 11/1990 | Greene | 623/38 |
| 5,013,325 | 5/1991 | Rennerfelt | 623/38 |
| 5,047,063 | 9/1991 | Chen | 623/38 |
| 5,116,382 | 5/1994 | Steinkamp et al. | |
| 5,326,352 | 7/1994 | Ferrier | 623/38 |

FOREIGN PATENT DOCUMENTS

| | | | |
|---|---|---|---|
| 0267347 | 11/1986 | European Pat. Off. | 623/38 |
| 1502061 | 10/1967 | France | 623/38 |
| 2123840 | 1/1972 | Germany | 623/38 |
| 2162069 | 7/1985 | United Kingdom | 623/38 |
| 2173569 | 4/1986 | United Kingdom | |
| 9317640 | 9/1993 | WIPO | 623/38 |

*Primary Examiner*—David H. Willse
*Assistant Examiner*—Bruce E. Snow
*Attorney, Agent, or Firm*—Reising, Ethington, Barnard, Perry & Milton

[57] ABSTRACT

A prosthetic connector assembly (10) for adjustably connecting a socket (22) with a prosthetic limb includes an end plate (12) having a top side (16), a bottom side (18), and a central opening (14) therein. A socket (22) extends upwardly from the top side (16) of the end plate (12) and an attachment member (66) is supported on the bottom side (18) thereof. An oblong washer (26) is disposed within the socket (22) and is supported by the top side (16) of the end plate (12). A bolt (84) extends through the attachment member (66), washer (26), and central opening (14) in the end plate (12) to retain the washer (26) and attachment member (66) against the end plate (12) while permitting relative adjustment of the attachment member (66) with respect to the end plate (12).

19 Claims, 3 Drawing Sheets

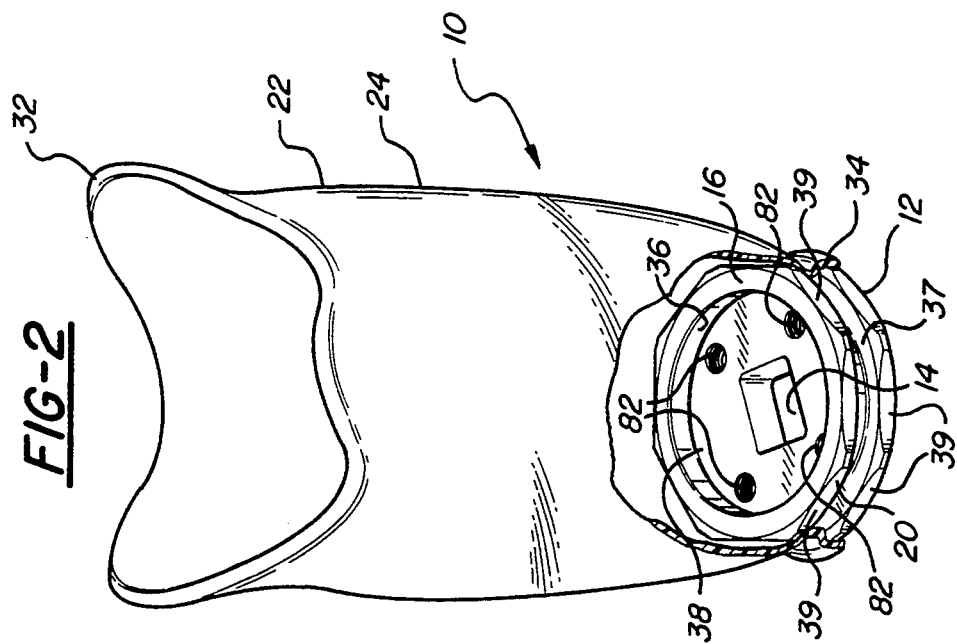
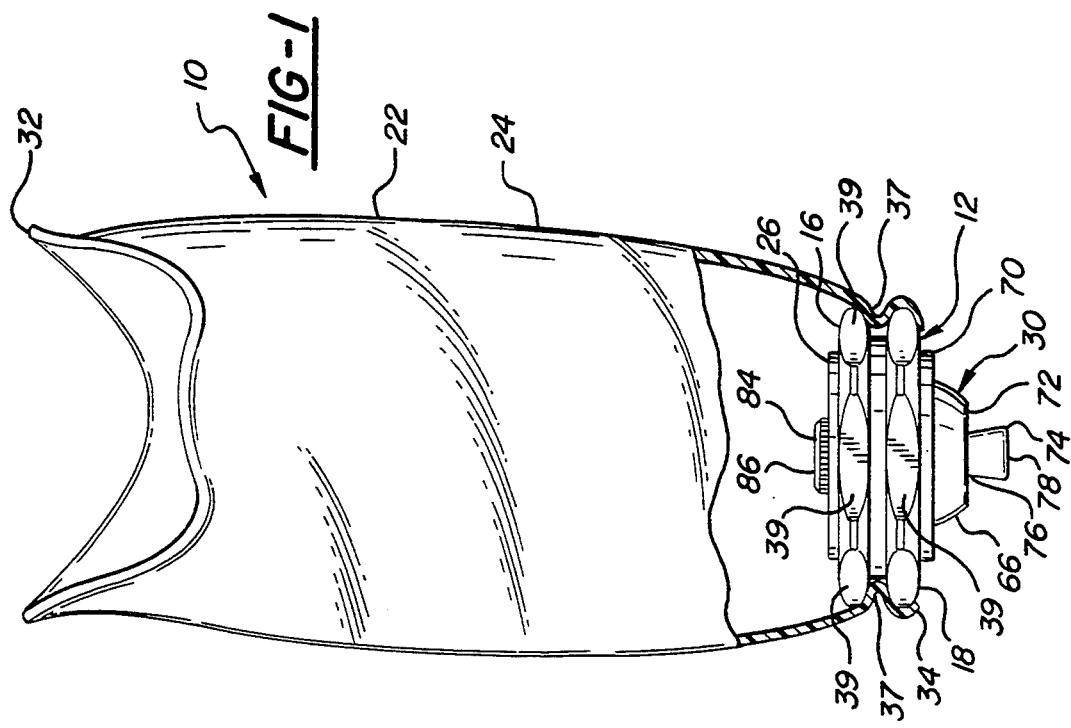

5,443,526

ADJUSTABLE PROSTHETIC CONNECTOR ASSEMBLY

TECHNICAL FIELD

The subject invention generally relates to a prosthetic connector assembly for providing relative adjustment between a prosthetic limb and a socket.

BACKGROUND ART

Prosthetic assemblies generally include a prosthetic limb and a socket which must be accurately positioned with respect to one another to achieve proper balance of the prosthetic limb. Depending upon the style, size, and weight of the prosthetic limb, the proper position with respect to the socket will vary. Early prosthetic assemblies comprised a prosthetic limb with a socket fixedly attached to the limb such that the relative positions of the limb and socket would be permanently set by the manufacturer.

Unfortunately, all users of prosthetic limbs are not built to the same proportions and small adjustments of the limb with respect to the socket are often necessary to achieve maximum comfort. In addition, prosthetic users often require a new socket due to a change in girth of the amputated stump. However, if the limb is permanently attached to the socket, the limb must also be replaced even though it is still satisfactory to the prosthetic user. Conversely, a prosthetic user may desire an updated limb and thus be forced to replace a comfortable and functional socket.

Therefore, newer prosthetic assemblies include separate limbs and sockets to allow a user to replace one without being forced to replace both. An adjustable connector assembly is provided to retain the socket and limb together and provide relative adjustment between the socket and limb. In this manner, limbs of varying design can be aligned perfectly with any socket to achieve proper balance and comfort.

Unfortunately, many modern connector assemblies are either very complex or provide a limited range of permissible adjustment. For example, U.S. Pat. No. 5,013,325 to Rennerfelt discloses a socket for a prosthetic assembly comprising an end plate and a cylindrical wall extending upwardly therefrom. A circular opening is disposed in the end plate, and a circular washer is disposed over the opening and against the end plate. A bolt extends through the washer and through the opening for attachment to a prosthetic limb. As the position of the limb is adjusted, the bolt and circular disc will move relative to the circular opening.

To achieve the maximum possible adjustment, the circular opening should be as large as possible to permit the bolt to have the widest range of movement. As the opening is expanded, however, the disc must also be expanded to remain larger than the opening. Unfortunately, the movement of the disc is restricted by the cylindrical wall of the socket and a large disc will have a small range of movement within the socket. Therefore, due to the competing constraints of disc size and opening size, maximum available adjustment is limited.

SUMMARY OF THE INVENTION AND ADVANTAGES

The subject invention generally relates to a prosthetic connector assembly for adjustably connecting a socket with a prosthetic limb. The connector assembly includes a plate member defining a first opening therein and having a top side, a bottom side, and an outer periphery. A socket comprises a wall member extending upwardly from the top side of the plate member and surrounds the first opening in spaced relation thereabout. A washer is disposed within the socket, extending across the first opening in the plate member and supported by the top side of the plate member. The washer includes a length and a width and is moveable within the socket in the direction of the width. The washer defines a second opening therein. Attachment means are included for joining a prosthetic limb adjacent the bottom side of the plate member to the washer while permitting relative movement of the washer and the limb with respect to the plate member. The invention is characterized by the length of the washer being greater than the width whereby the larger length permits the washer to span a large first opening in the plate member while remaining supported on the top surface thereof and the smaller width permits a greater range of movement within the socket in the direction of the width.

The subject invention is advantageous by permitting a greater range of adjustment between the limb and the socket than previously possible. The opening in the plate member can be made large to maximize the range of movement of the limb, and a washer having a large length can be utilized to span the large opening. However, the smaller width of the washer will permit movement of the washer in the direction of the width without being restricted by the walls of the socket.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a side view of the prosthetic connector assembly of the present invention;

FIG. 2 is a top perspective view of the socket and the plate member;

DETAILED DESCRIPTION OF THE PREFERRED EMBODIMENT

Figure 3:
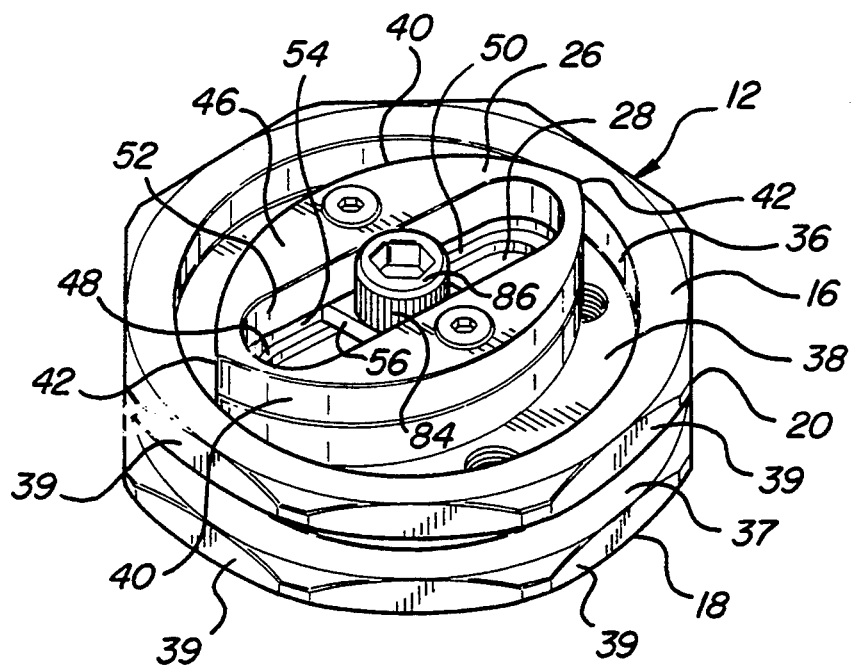
FIG. 3 is a top perspective view of the plate member and the washer.

A prosthetic connector assembly for adjustably connecting a socket with a prosthetic limb is generally shown at 10 in FIG. 1. The connector assembly 10 includes a plate member 12 defining a first opening 14 therein and having a top side 16, a bottom side 18, and an outer periphery 20. A socket 22 is disposed on the plate member 12 and comprises a wall member 24 extending upwardly from the top side 16 of the plate member 12 and surrounding the first opening 14 in spaced relation thereabout. A washer 26 is disposed within the socket 22, extending across the first opening 14 in the plate member 12 and supported by the top side 16 of the plate member 12. The washer 20 includes a length L and a width W and is moveable within the socket 22 in the direction of the width W. The washer 26 defines a second opening 28 therein. Attachment means 30 are included for joining a prosthetic limb (not shown) adjacent the bottom side 18 of the plate member 12 to the washer 26 while permitting relative movement of the washer 26 and the limb with respect to the plate member 12. The invention is characterized by the length L of the washer 26 being greater than the width W whereby the larger length L permits the washer 26 to span a large first opening 14 in the plate member 12 while remaining supported on the top side 16 thereof and the smaller width W permits a greater range of movement within the socket 22 in the direction of the width W.

The socket 22 comprises a rigid plastic member extending upwardly from the plate member 12 adjacent the outer periphery 20 thereof. More specifically, the socket 22 surrounds the outer periphery of the plate member 12 in roughly cylindrical fashion. The wall member 24 of the socket 22 includes a top edge 32 and a bottom edge 34, and the bottom edge 34 is flush with the bottom side 18 of the plate member 12.

The socket 22 is preferably formed to approximate the shape of the amputee's stump. However, to provide a more comfortable fit, a flexible plastic sleeve (not shown) can be inserted within the socket 22 to provide a more precise fit of the socket to an amputee's stump. The sleeve can include a rounded end portion and padding to provide maximum comfort. The sleeve can thus permit inexpensive adjustments to be made in the fit of the socket 22 without replacing the entire socket 22.

As shown in FIG. 2, the plate member 12 comprises a roughly circular member including a flat top side 16 and a flat bottom side 18. The first opening 14 is disposed through the center of the plate member 12 and is square, although any shape such as circular, hexagonal, or octagonal would be appropriate. A circular raised rim 36 is supported by the top side 16 of the plate member 12 and extends upwardly therefrom. Preferably, the rim 36 is disposed adjacent the outer periphery 20 of the plate member 12 and within the wall member 24 of the socket 22. The rim 36 abuts against the wall member 24 and extends upwardly only a relatively small amount compared to the height of the wall member 24 of the socket 22. The rim 36 is equidistant from the center of the first opening 14 in the plate member 12 such that the first opening 14 is in the center of the raised rim 36. The raised rim 36 and the bottom side 18 of the plate member 12 thus define a circular recess 38 having a constant diameter. The raised rim 36 could also define an oblong or irregularly shaped recess having a maximum diameter and a minimum diameter.

Figure 4:
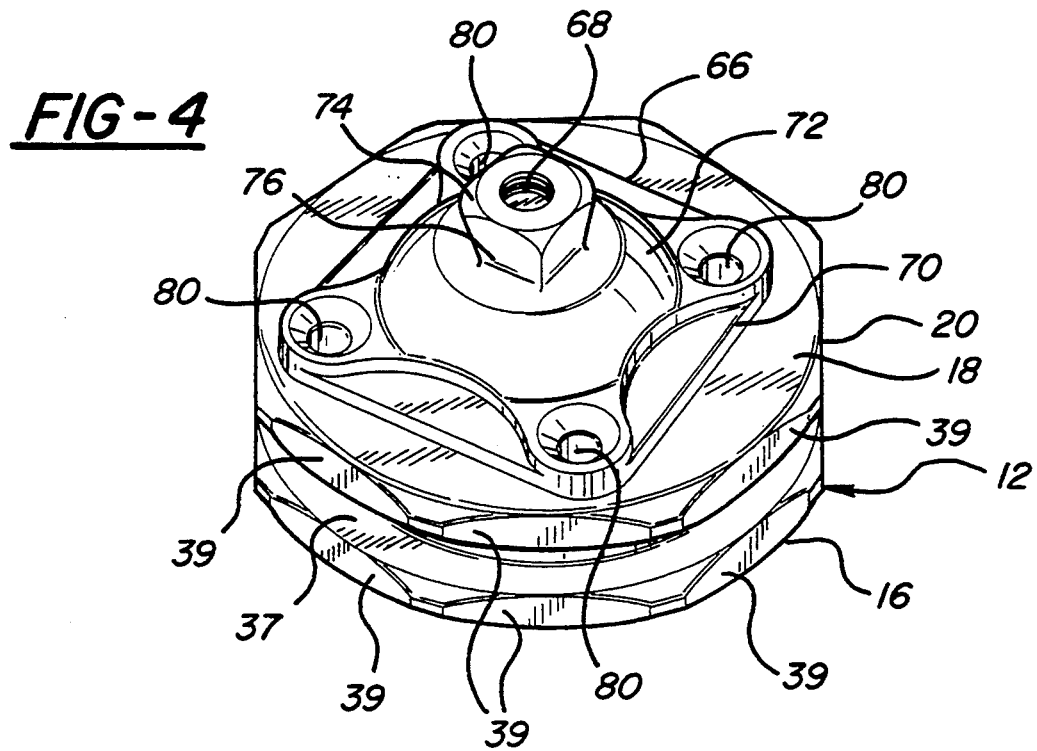
FIG. 4 is a bottom perspective view of the plate member and the attachment member.

As shown in FIGS. 3 and 4, the plate member 12 includes a retaining groove 37 with a portion of the wall member 24 of the socket 22 molded and form fitted therewithin. In this manner, the socket 22 will be securely joined to the plate member 12. In addition, the plate member 12 includes a plurality of intermittent flat faces 39 along the outer periphery 20 thereof. By molding the socket 22 tightly about the faces 39, rotational movement of the socket 22 with respect to the plate member 12 is prevented.

Figure 5:
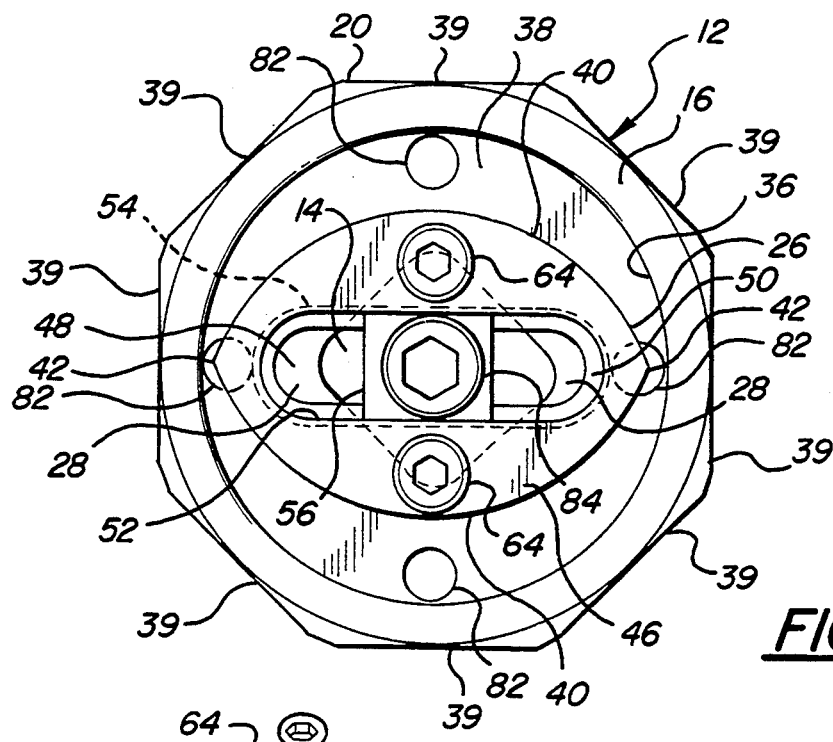
FIG. 5 is a top view of the plate member and the washer.
Figure 6:
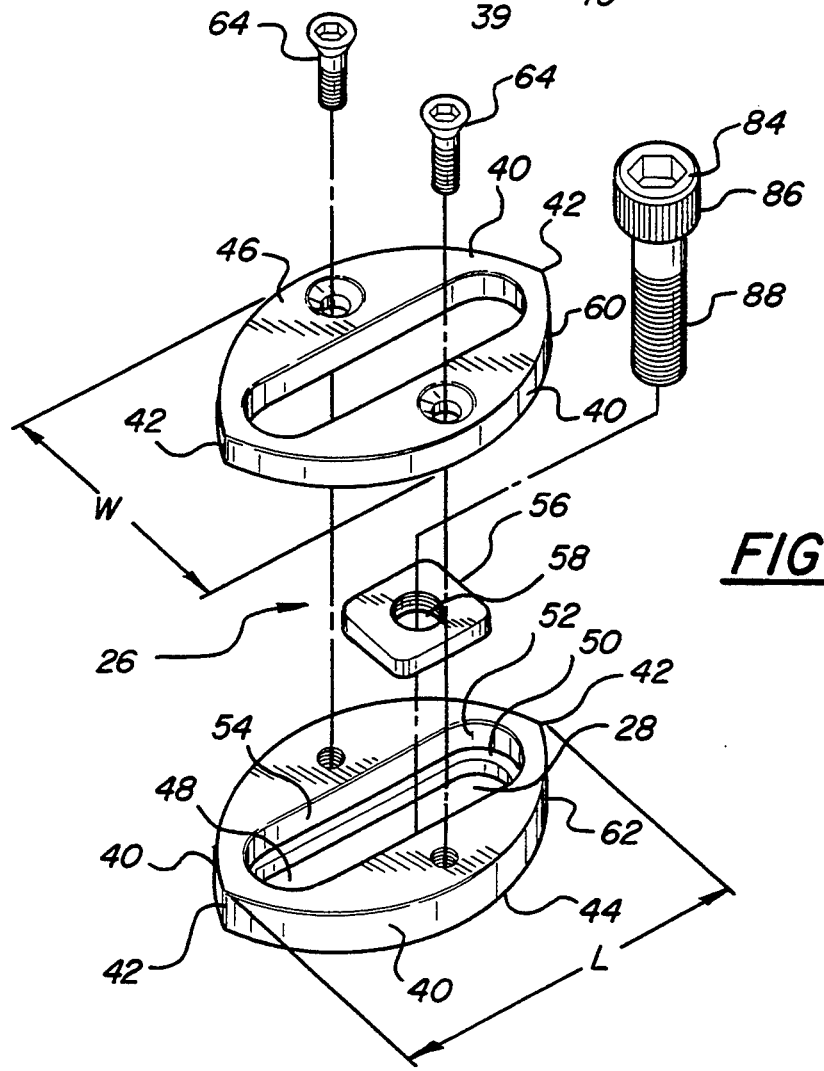
FIG. 6 is an exploded view of the washer.

As shown best in FIGS. 3, 5, and 6, the washer 26 is preferably almond shaped, having two symmetrical curved sides 40 meeting to form two pointed ends 42. As stated above, the washer has a length L longer than its width W to thereby form an oblong cross-section. However, many different shapes of the washer 26 are permissible, including a rectangle, oval, or an irregular or asymmetrical shape as long as the washer has two perpendicular dimensions (e.g. length and width) with one of the dimensions being larger than the other. The washer 26 is disposed within the circular recess 38 defined by the raised rim 36 and is thus disposed within the socket 22.

The washer 26 includes a bottom face 44 supported by the top side 16 of the plate member 12 and a top face 46. The washer 26 includes a longitudinal recess 48 disposed therein and including a bottom surface 50 and a wall surface 52 extending upwardly from the bottom surface 50. The second opening 28 comprises a longitudinal slot 28 extending through the bottom surface 50 of the recess 48 and through the bottom face 52 of the washer 26. Both the longitudinal recess 48 and slot 28 are parallel to the length L of the washer 26. A groove 54 is disposed within the wall surface 52 of the longitudinal recess 48 extending parallel to the bottom surface 50 of the recess 48. A nut 56 is supported within the groove 54 for slidable movement along the longitudinal recess 48 and includes a threaded opening 58.

The washer 26 comprises a top half 60 and a bottom half 62 joined together by screws 64, as best shown in FIG. 6. By separating the two halves 60,62, the nut 56 can be installed within the groove 54. Thus, the groove 54 cannot be completely disposed in only one of the two halves 60,62 but must be formed at least in part by both halves 60,62 of the washer 26.

The attachment means 30 is illustrated in FIG. 4 and includes an attachment member 66 disposed adjacent the bottom side 18 of the plate member 12 and extending outwardly therefrom for attachment to a prosthetic limb. The attachment member 66 defines a third opening 68 disposed therethrough and includes a base plate 70, a hemispherical portion 72 extending outwardly from the base plate 70, and a truncated pyramidal attachment nub 74 extending outwardly from the hemispherical portion 72. The nub 74 includes a narrow base 76 attached to the hemispherical portion 72 and a wider tip 78 extending freely therefrom. The base plate 70 of the attachment member 66 includes a flat bottom surface (not shown) disposed flush with the flat bottom side 18 of the plate member 12.

The attachment member 66 also includes four holes 80, and four corresponding holes 82 are disposed in the plate member 12. The holes 80,82 permit the attachment member 66 to be permanently fixed in a centered location with respect to the plate member 12. In this manner, prosthetics which require the attachment member 66 to be perfectly centered can be accommodated.

The attachment means 30 includes a bolt 84, as shown in FIGS. 3 and 6, which includes a head 86 and a threaded shank 88. The bolt 84 is inserted through the first, second, and third openings 14,28,68 and through the threaded opening 58 in the nut 56 to retain the washer 26 and attachment member 66 in place against the plate member 12. The shank 88 of the bolt 84 can be first inserted through either the third opening 68 in the attachment member 66 or the second opening 28 in the washer 26. By first inserting the shank 88 through the third opening 68, the head 86 of the bolt 84 will be disposed adjacent the attachment member 66. This arrangement is advantageous in that the bolt 84 can be loosened for adjusting the position of the attachment member 66 without removing the socket 22 from the user.

However, the bolt head 86 may interfere with the proper connection of a prosthetic limb (not shown) to the attachment member 66. In this case, the shank 88 would first be inserted through the second opening 68 in the washer 26 whereby the head 86 would remain inside the socket 22 and adjacent the washer 26. The length of the shank 88 can be selected such that the shank 88 will not extend outwardly from the third opening 68 in the attachment member 66. The bolt head 86 will generally rest against the nut 56, but in embodiments without a nut 56 the bolt head 86 will rest against the bottom surface 50 of the recess 48 within the washer 26.

In operation, whenever adjustment of the attachment member 66 is desired, the bolt 84 is loosened and the attachment member 66 and washer 26 are permitted to move freely with respect to the plate member 12. The bolt 84 is maintained within the first, second, and third openings 14,28,68 such that any movement by the attachment member 66 and the limb is mirrored by the washer 26. Thus, the range of movement of the attachment member 66 is limited by the range of movement of the washer 26 within the circular recess 38 defined by the raised rim 36. For adjustment in the direction of the length L of the washer 26, the bolt 84 can slide within the longitudinal slot 28 and longitudinal recess 48. In addition, if the length L is smaller than the diameter of the circular recess 38, the washer 26 itself can move with respect to the plate member 12. To achieve adjustment in the direction of the width W, the washer 26 can merely be moved in the direction of the width W.

Because the washer 26 has a large length L, the washer 26 can span a first opening 14 in the plate member 12 that is almost as large as the diameter of the circular recess 38. The smaller width W, however, permits the washer 26 to move in the direction of the width W without striking the raised rim 36.

Even if the washer 26 did not contain a longitudinal slot 28, adjustment in any direction could still be accomplished. The smaller width W would still permit adjustment in one direction, and the washer 26 could merely be rotated to change the orientation of the small width W with respect to the plate member 12 and permit adjustment in any direction.

Other arrangements are also possible in which the recess 38 defined by the raised rim 36 is square and the washer 26 comprises a rectangle. The washer 26 could then slide in the direction of its width W, and the longitudinal slot 28 would permit adjustment in the direction of the length L. Rotation of the washer 26, however, would not be possible.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A prosthetic connector assembly (10) for adjustably connecting a socket (22) with a prosthetic limb, said connector assembly (10) comprising:
   a plate member (12) including a top side (16), a bottom side (18), and an outer periphery (20);
   said plate member (12) defining a first opening (14) disposed therethrough;
   a socket (22) including a wall member (24) extending upwardly from said top side (16) of said plate member (12) and surrounding said first opening (14) in spaced relation thereabout;
   a washer (26) disposed within said socket (22), extending across said first opening (14) in said plate member (12) and supported by said top side (16) of said plate member (12);
   said washer (26) including a length (L) and a width (W) and being moveable within said socket (22) in the direction of said width (W);
   said washer (26) including a top surface (46);
   said washer (26) including an inner wall surface (52) defining a longitudinal opening (48) in said washer (26);
   said inner wall surface (52) including a groove (54) disposed therein and spaced below said top surface (46) of said washer (26);
   an attachment member (30) for joining a prosthetic limb adjacent said bottom side (18) of said plate member (12) to said washer (26) while permitting relative movement of said washer (26) and the limb with respect to said plate member (12); and
   characterized by a nut (56) slidably disposed within said groove (54) and securely retained therein to remain attached to said washer (26) while supporting a bolt (84) in slidable lateral adjustment with respect to said washer (26).

2. An assembly (10) as set forth in claim 1 further characterized by said plate member (12) being circular.

3. An assembly (10) as set forth in claim 1 further characterized by said plate member (12) being flat.

4. An assembly (10) as set forth in claim 1 further characterized by said first opening (14) in said plate member (12) being disposed in the center of said plate member (12).

5. An assembly (10) as set forth in claim 1 further characterized by said first opening (14) in said plate member (12) being square.

6. An assembly (10) as set forth in claim 1 further characterized by said first opening (14) in said plate member (12) being circular.

7. An assembly (10) as set forth in claim 1 further characterized by said washer (26) having an almond shape.

8. An assembly (10) as set forth in claim 1 further characterized by said attachment means (30) including an attachment member (66) disposed adjacent said bottom side (18) of said plate member (12) and extending outwardly therefrom.

9. An assembly (10) as set forth in claim 8 further characterized by said attachment member (66) defining a third opening (68) therethrough.

10. An assembly (10) as set forth in claim 9 further characterized by said third opening (68) in said attachment member (66) including a threaded passage (68) extending therethrough.

11. An assembly (10) as set forth in claim 10 further characterized by said attachment means (30) including a bolt (84).

12. An assembly (10) as set forth in claim 11 wherein said bolt (84) includes a head (86).

13. An assembly (10) as set forth in claim 12 wherein said bolt (84) includes a threaded shank (88), further characterized by said threaded shank (88) being disposed within said threaded passage (68) in said third opening (68).

14. An assembly (10) as set forth in claim 13 further characterized by said nut (56) including a threaded opening (58) surrounding said threaded shank (88) of said bolt (84).

15. An assembly (10) as set forth in claim 1 wherein said wall member (24) of said socket (22) includes an inner surface and an outer surface, further characterized by said plate member (12) including a raised rim (36) disposed adjacent said outer periphery (20) of said plate member (12) and adjacent said inner surface of said wall member (24).

16. An assembly (10) as set forth in claim 15 wherein said socket (22) includes a minimum inner diameter, further characterized by said length (L) of said washer (26) being smaller than said minimum inner diameter of said socket (22).

17. An assembly (10) as set forth in claim 16 wherein said raised rim includes a minimum inner diameter, further characterized by said length (L) of said washer (26) being smaller than said minimum inner diameter of said raised rim (36).

18. An assembly (10) as set forth in claim 8 further characterized by said attachment member (66) including a base portion (70) supported on said bottom side (18) of said plate member (12).

19. An assembly (10) as set forth in claim 18 further characterized by said attachment member (66) including a connection nub (74) extending outwardly from said base portion (70).

* * * * *